(12) United States Patent
Yam et al.

(10) Patent No.: US 7,572,912 B2
(45) Date of Patent: Aug. 11, 2009

(54) LUMINESCENT GOLD (III) COMPOUNDS, THEIR PREPARATION, AND LIGHT-EMITTING DEVICES CONTAINING SAME

(75) Inventors: Vivian Wing-Wah Yam, Hong Kong (CN); Man-Chung Wong, Hong Kong (CN); Hoi-Sing Kwok, Hong Kong (CN); Xiuling Zhu, Hong Kong (CN)

(73) Assignee: University of Hong Kong, Hong Kong (CN)

( * ) Notice: Subject to any disclaimer, the term of this patent is extended or adjusted under 35 U.S.C. 154(b) by 422 days.

(21) Appl. No.: 10/977,200

(22) Filed: Oct. 29, 2004

(65) Prior Publication Data

US 2006/0091378 A1 May 4, 2006

(51) Int. Cl.
*C07F 1/12* (2006.01)
*C09K 11/58* (2006.01)
(52) U.S. Cl. ............... 546/2; 252/301.16; 252/301.26; 428/690; 428/917
(58) Field of Classification Search ............... 546/2; 252/301.16, 301.26; 502/150, 171, 344; 428/690, 917
See application file for complete search history.

(56) References Cited

U.S. PATENT DOCUMENTS

2003/0040627 A1 2/2003 Fujii

OTHER PUBLICATIONS

J.H. Burroughs, et al., "Light-emitting diodes based on conjugated polymers," Nature vol. 347, Oct. 1990, pp. 539-541.
D. Braun, et al., "Visible light emission from semiconducting polymer diodes," Appl. Phys. Lett. (18) May 1991, pp. 1982-1984.
W. Helfrich, et al., "Recombination Radiation in Anthracene Crystals," Physical Review Letters, vol. 14, No. 7, Feb. 1976, p. 229-231.
C.W. Tang, et al., "Organic electroluminescent diodes," Appl. Phys. Letter 51 (12), Sep. 1987, pp. 913-915.
M.A. Baldo, et al., "Highly efficient phosphorescent emission from organic electroluminescent devices," Nature, vo. 395, Sep. 1998, pp. 151-154.
M.A. Baldo, et al., "Very high-efficiency green organic light-emitting devices based on electrophosphorescence," Applied Physics Letters, vol. 75, No. 1, Jul. 19999, pp. 4-6.
M.A. Baldo, et al., "High-efficiency fluorescent organic ligh-emitting devices using a phosphorescent sensitizer," Nature, vol. 403, Feb. 2000, pp. 750-753.
S. Welter, et al., "Electroluminescent device with reversible switching between red and green emission," Nature, vol. 421, Jan. 2003, pp. 54-57.

Vadim Adamovich, et al., "High efficiency single dopant white electrophosphorescent light emitting diodes," New J. Chem., 2002, 26, pp. 1171-1178.
Maria Agostina Cinellu, et al., Replacement of the chloride ligand in [Au(C,N,N)Cl][PF$_6$], J. Chem. Soc., Dalton Trans., 1999, pp. 2823-2831.
Vivian Wing-Wah Yam, et al., "Syntheses, Crystal STructures and Photophysics of Organogold(III) Diimine Complexes," J. Chem. Soc. Dalton Trans. 19993, pp. 1001-1002.
Kar-Ho Wong, et al., "Application of 2,6-Diphenylpyridine as a Tridentate [CNC] Dianionic Ligand in Organogold (III) Chemistry Structural and Spectroscopic Properties of Mono-and Binuclear Transmetalated Gold (III) Complexes," Organometallics 1998, 17, pp. 3505-3511.

*Primary Examiner*—Charanjit S Aulakh
(74) *Attorney, Agent, or Firm*—Robert D. Katz; Cooper & Dunham LLP

(57) ABSTRACT

A class of luminescent gold(III) compounds with a tridentate ligand and at least one strong σ-donating group having the chemical structure represented by the general formula (I):

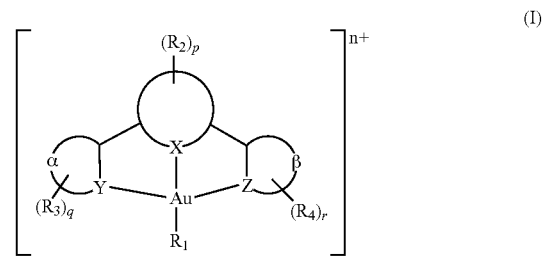

wherein $R_1$-$R_4$ each independently represent the group containing hydrogen, halogen, alkynyl, substituted alkynyl, alkyl, substituted alkyl, aryl, substituted aryl, heteroaryl, substituted heteroaryl, alkoxyl, substituted alkoxyl, amino, substituted amino, cyano, nitro, alkylcarbonyl, alkoxycarbonyl, arylcarbonyl, aryloxycarbonyl, mono- or dialkylaminocarbonyl, alkylcarbonyloxy, arylcarbonyloxy, aryloxy, alkoxycarbonyl, aryloxycarbonyloxy group, and the like; X, Y and Z each independently represent a heteroatom or a carbon;

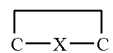

represents an aromatic or heterocyclic 5- or 6-membered ring; α and β each independently represent a bridge for an aromatic or heterocyclic 5- or 6-membered ring or represent a break for non-cyclic moiety; C—X, C—Y and C—Z each independently represent a single bond or double bond; n represents a zero or an integer; p, q and r represent positive integers.

18 Claims, 12 Drawing Sheets

LUMINESCENT GOLD (III) COMPOUNDS, THEIR PREPARATION, AND LIGHT-EMITTING DEVICES CONTAINING SAME

CROSS-REFERENCES TO RELATED APPLICATIONS

Not Applicable.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISK

Not Applicable.

BACKGROUND OF THE INVENTION (1) Field of the Invention

The present invention is directed to a new class of luminescent gold(III) compounds containing a tridentate ligand and having at least one strong σ-donating group. Such compounds can be used as light-emitting material in phosphorescence based organic light-emitting devices (OLEDs), wherein different colors can be obtained by varying the applied DC voltage or the dopant concentration of said compounds.

(2) Description of Related Art Including Information Disclosed Under 37 C.F.R. 1.97 and 1.98.

The market for flat-panel displays has attracted considerable attention in connection with the development of electroluminescent materials. The electroluminescence materials used are generally categorized into conjugated polymers or low-molar-mass small molecules. OLEDs are among the most important candidates for the use of electroluminescent materials in commercial flat-panel displays because OLEDs possess the advantages of robustness, ease of fabrication and color tuning, wide viewing angle, high brightness and contrast ratios, low turn-on voltage and low energy consumption.

A typical OLED structure is composed of a thin film of organic material sandwiched between a transparent conductor such as indium tin oxide (ITO), and a vapor deposited metal cathode. Upon applying an electrical potential, excitons are formed by the recombination of the holes and electrons, injected from the ITO electrode and metal cathode, respectively. Electroluminescence is generated in the organic material from the radiative relaxation of excitons. Higher performance of the device can be achieved by using multiple organic layers for separation of hole and electron transporting layers.

Although electroluminescence from organic polymers was initially reported years ago [Kaneto, K.; Yoshino, K.; Koa, K.; Inuishi, Y. *Jpn. J. Appl. Phys.* 18, 1023 (1974)], it was only after the report on yellow-green electroluminescence from poly(p-phenylenevinylene) (PPV) that light-emitting polymers and OLEDs have received much attention [Burroughs, J. H.; Bradley, D. D. C.; Brown, A. R.; Marks, N.; Friend, R. H.; Burn, P. L.; Holmes, A. B., *Nature* 347, 539 (1990)]. Later on, similar studies were reported by using PPV derivatives as the light-emitting polymers [Braun, D.; Heeger, A. J., *Appl. Phys. Lett.* 58, 1982 (1991)]. Since then a number of new electroluminescent polymers have been investigated for improved properties.

Electroluminescence of organic materials was discovered in anthracene crystals immersed in liquid electrolyte in 1965 [Helfrich, W.; Schneider, W. G. *Phys. Rev. Lett.* 14, 229 (1965)]. Although lower operating voltages could be achieved by using a thin film of anthracene as well as solid electrodes, very low efficiency of such a single-layer device was encountered. High-performance green electroluminescence from an organic small molecule, aluminum tris(quinolate) ($Alq_3$), was first reported in 1987 [Tang, C. W.; VanSlyke, S. A. *Appl. Phys. Lett.* 51, 913 (1987)]. A double-layer OLED with high efficiency and low operating voltage was described, in which $Alq_3$ was utilized both as emitting layer and electron transporting layer. Subsequent modifications of the device with triple-layer structure gave better performance with higher efficiency.

Some improvements in OLED efficiencies have been achieved by using phosphorescent material to generate light emission from both singlet and triplet excitons. One approach, particularly for small-molecule OLEDs, is to harvest triplet excitons efficiently through incorporation of heavy metal centers, which would increase spin-orbit coupling and hence intersystem crossing into the triplet state. In 1998, Baldo et al. demonstrated a phosphorescence electroluminescence device with high quantum efficiency by using platinum(II) 2,3,7,8,12,13,17,18-octaethyl-21H,23H-porphine (PtOEP) as a dye [Baldo, M. A.; O'Brien, D. F.; You, Y.; Shoustikow, A.; Sibley, S.; Thompson, M. E.; Forrest, S. R. *Nature* 395, 151 (1998)]. A multilayer device in which the emitting layer of $Alq_3$ is doped with PtOEP showed a strong emission at 650 nm attributed to the triplet excitons of PtOEP. Cyclometalated iridium(III) is known to show phosphorescence and is another class of materials used for high efficiency OLEDs. Baldo et al. reported the use of fac-tri(2-phenylpyridine)iridium(III) [$Ir(ppy)_3$] as phosphorescence emitting material which was doped in 4,4'-N,N'-dicarbazole-biphenyl (CBP) as a host in an OLED to give high quantum efficiency [Baldo, M. A.; Lamansky, S.; Burrows, P. E.; Thompson, M. E.; Forrest, S. R. *Appl. Phys. Lett.* 75, 4 (1999)]. In addition, fac-tri(2-phenylpyridine)iridium(III) [$Ir(ppy)_3$] was used as phosphorescence sensitizer for high efficiency fluorescent OLED [Baldo, M. A.; Thompson, M. E.; Forrest, S. R. *Nature*, 403, 750 (2000)]. Using the concept of a phosphorescence emitter with a higher population of excitions, very high efficiency red fluorescence from [2-methyl-6-[2-(2,3,6,7-tetrahydro-1H,5H-benzo[II]quinolizin-9-yl)-ethenyl]-4H-pyran-4-ylidene]propanedinitrile (DCM2) was found in a multilayer OLED composed of $Ir(ppy)_3$ and DCM2 dopant layers. In a sensitization process, energy is transferred from $Ir(ppy)_3$ to DCM2 to give such high efficiency fluorescence.

Apart from the enhancement of the emission efficiency, the ability to bring about a variation in the emission color would be important. Most of the common approaches involve the use of different light-emitting materials or multi-component blended mixtures of light-emitting materials with different emission characteristics for color tuning. Examples that employ a single light-emitting material as dopant to generate more than one emission color have been rare. Recent studies have shown that different emission colors from a single emissive dopant could be generated by using phosphorescent material through a change in the direction of the bias or in the dopant concentration. Welter et al. reported the fabrication of a simple OLED consisting of semiconducting polymer PPV and phosphorescent ruthenium polypyridine dopant [Welter, S.; Krunner, K.; Hofstraat, J. W.; De Cola, D. *Nature*, 421, 54 (2003)]. At forward bias, red emission from the excited state of the phosphorescent ruthenium polypyridine dopant was observed, while the OLED emitted a green emission at reverse bias in that the lowest excited singlet state of PPV was populated. Adamovich et al. reported the use of a series of phosphorescent platinum(II) [2-(4,6-difluorophenyl)pyridinato-N,C²'] β-diketonates as single emissive dopant in OLED [Adamovich, V.; Brooks, J.; Tamayo, A.; Alexander, A. M.; Djurovich, P. R.; D'Andrade, B. W.; Adachi, C.; Forrest, S. R.; Thompson, M. E. *New. J. Chem.* 26, 1171 (2002)]. Both blue emission from the monomeric species and orange emission from the aggregates were observed in such OLED and the relative intensity of the orange emission increases as the doping level is increased. As a result, the electroluminescence color can be tuned by changing the dopant concentration, and white illumination sources of an OLED can be obtained in a doping concentration with equal intensities of the monomeric and aggregate bands. In both cases, the change of electroluminescence color in OLED can be accomplished upon a variation of the external stimulus or fabrication conditions while keeping the light-emitting material the same.

Despite recent interest in electrophosphorescent materials, in particular metal complexes with heavy metal centers, most of the work has been focused on the use of iridium(III), platinum(II) and ruthenium(II), while other metal centers have been relatively less extensively explored. In contrast to the isoelectronic platinum(II) compounds which are known to show rich luminescence properties, very few examples of luminescent gold(III) compounds have been reported, probably due to the presence of low-energy d-d ligand field (LF) states and the electrophilicity of the gold(III) metal center. The introduction of strong σ-donating ligands into gold(III) compounds to enhance the luminescence properties as a result of the enlargement of d-d splitting has been considered. Yam et al. first demonstrated that gold(III) aryl compounds are photo-stable and are capable of displaying interesting photoluminescence properties which occur even at room temperature [Yam, V. W. W.; Choi, S. W. K.; Lai, T. F.; Lee, W. K. *J. Chem. Soc., Dalton Trans.* 1001(1993)]. Another interesting donor ligand is the alkynyl group. But despite the fact that a number of gold(I) alkynyls are known and have been shown to exhibit interesting luminescence properties, the chemistry of gold(III) alkynyls has been essentially ignored, except for a brief report on the synthesis of an alkynylgold(III) compound of 6-benzyl-2,2'-bipyridine in the literature [Cinellu, M. A.; Minghetti, G.; Pinna, M. V.; Stoccoro, S.; Zucca, A.; Manassero, M. *J. Chem. Soc. Dalton Trans.* 2823 (1999)], but their luminescence behaviour has remained totally unexplored. The present inventors have described herein the design, synthesis and photoluminescence behaviors of luminescent gold(III) compounds with a tridentate ligand and at least one strong σ-donating group, and the use of such compounds as electrophosphorescent material in OLEDs to give strong electroluminescence with high efficiency.

BRIEF SUMMARY OF THE INVENTION

The present invention is directed to novel luminescent gold(III) compounds, their preparation, and OLEDs containing them. The compounds have the chemical structure shown in generic formula (I):

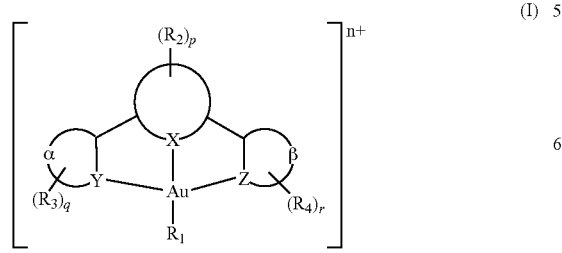

wherein $R_1$, $R_2$, $R_3$ and $R_4$ each independently represents a substituent selected from the group consisting of hydrogen, halogen, alkynyl, substituted alkynyl, alkyl, substituted alkyl, aryl, substituted aryl, heteroaryl, substituted heteroaryl, alkoxyl, substituted alkoxyl, amino, substituted amino, cyano, nitro, alkylcarbonyl, alkoxycarbonyl, arylcarbonyl, aryloxycarbonyl, mono- or dialkylaminocarbonyl, alkylcarbonyloxy, arylcarbonyloxy, aryloxy, alkoxycarbonyl, aryloxycarbonyloxy group, and the like; X, Y and Z each independently represent a heteroatom or a carbon;

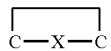

represents an aromatic or heterocyclic 5- or 6-membered ring; α and β each independently represents a bridge for an aromatic or heterocyclic 5- or 6-membered ring, or a break for a non-cyclic moiety; C—X, C—Y and C—Z each independently represents a single bond or double bond; n is a zero or an integer; and p, q and r are positive integers. The compounds of the present invention each contains one tridentate ligand and at least one strong σ-donating group coordinating to a gold(III) metal center.

The luminescent gold(III) compounds of the present invention show photoluminescence via triplet excited state upon photo-excitation, or electroluminescence via triplet exciton upon applying a DC voltage. Preferred compounds of the invention are thermally stable and volatile enough to be able to form a thin layer by sublimation or vacuum deposition.

The present invention is also directed to the use of luminescent compounds of general formula (I) as phosphorescent emitters or dopants fabricated into OLEDs to generate electroluminescence. In one embodiment, the light-emitting material used as a phosphorescent emitter or dopant in an OLED can comprise a gold(III) compound coordinated with one tridentate ligand and at least one strong σ-donating ligand.

In an OLED according to the present invention, the luminescent compound is included in a light-emitting layer or as a dopant arranged between a pair of electrodes. The typical structure of an OLED using the luminescent compound of the present invention as a light-emitting layer without an electron blocking layer is in the order shown in FIG. 1: anode/hole transporting layer/luminescent gold(III) compound as a light-emitting layer/electron injection layer/cathode.

The typical structure of an OLED using the luminescent compound of the present invention as a light-emitting layer with an electron blocking layer is in the order shown in FIG. 2: anode/hole transporting layer/luminescent gold(III) compound as light-emitting layer/hole blocking layer/electron injection layer/cathode.

The typical structure of an OLED using the luminescent compound of the present invention as a dopant with an electron blocking layer is in the order shown in FIG. 3: anode/hole transporting layer/luminescent gold(III) compound doped in host/hole blocking layer/electron transporting layer/cathode.

DETAILED DESCRIPTION OF THE INVENTION

Figure 1:
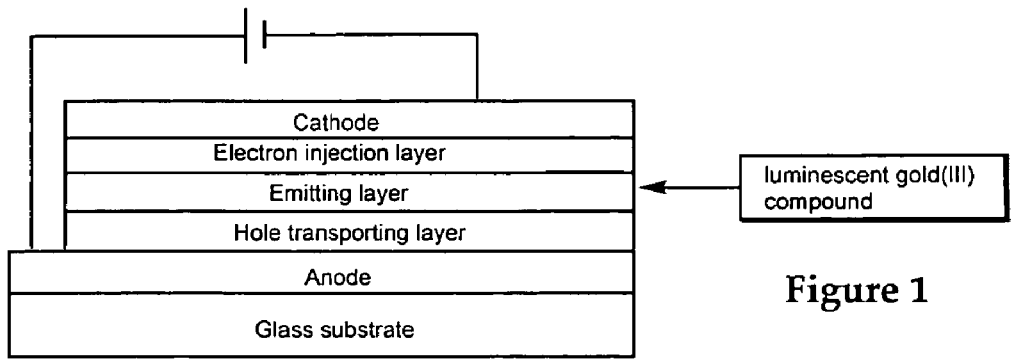
FIG. 1 shows the structure of an OLED using the luminescent compound of the present invention as the light-emitting layer without an electron blocking layer.

The present invention is related to the syntheses, spectral characterization, and luminescence properties of a class of luminescent gold(III) compounds with one tridentate ligand and at least one strong σ-donating group; and the use of such compounds as light-emitting material in OLEDs to provide electroluminescence with high efficiency and brightness. The compounds have the following structural characteristics:

(1) at least one gold metal center at an oxidation state of +3;
(2) said one gold metal center having four coordination sites;
(3) one tridentate ligand with one to three aromatic or heterocyclic ring(s) coordinating to the gold metal center;
(4) one monodentate ligand coordinating to the gold metal center;
(5) at least one strong σ-donating ligand coordinating to the gold metal center; and
(6) the compounds being charged or neutral.

Gold(III) compounds have been rarely observed to emit, in contrast to their isoelectronic platinum(II) compounds which are known to display rich luminescence properties. The lack of luminescence behavior in gold(III) compounds may be due to the presence of low-lying d-d ligand field (LF) states and the electrophilicity of the gold(III) metal center. Gold(III) aryl compounds [Yam, V. W. W.; Choi, S. W. K.; Lai, T. F.; Lee, W. K. *J. Chem. Soc., Dalton Trans.* 1001(1993)] are exceptions in that they show interesting luminescence properties even at room temperature and possess photo-stability upon light irradiation. Without wishing to be bound by theory, it is believed that the coupling of strong σ-donating ligands to gold(III) renders the metal centre more electron-rich, thereby raising the energy of the d-d states, which results in an improvement or enhancement of the luminescence by increasing the chances for population of the emissive state. A class of luminescent gold(III) compounds with one tridentate ligand and at least one strong σ-donating group will be described in detail hereinbelow.

The luminescent gold(III) compounds of the present invention can be formed into thin films by vacuum deposition, spin-coating or other known fabrication methods. Different multilayer OLEDs have been fabricated using the compounds of the present invention as light-emitting material or as dopant in the emitting layer. In general, the OLEDs consist of one anode and one cathode, between which are the hole transporting layer, light-emitting layer, and electron transporting or injection layer.

The present invention will be illustrated more specifically by the following non-limiting examples, it being understood that changes and variations can be made therein without deviating from the scope and the spirit of the invention as hereinafter claimed.

EXAMPLE 1

Synthesis and Characterization

Compounds 1-8 were synthesized according to the following methodology. The precursor compound, [Au(C^N^C)Cl], was prepared according to the modification of a procedure reported in the literature [Wong, K. H.; Cheung, K. K.; Chan, M. C. W.; Che, C. M. *Organometallics*, 17, 5305(1998)]. The desired compounds were synthesized by the reaction of [Au(C^N^C)Cl] with various alkynes in the presence of a base or copper catalyst in an organic solvent. For example, to a mixture of [Au(C^N^C)Cl], terminal alkyne and Et$_3$N in degassed dichloromethane solution was added CuI. The reaction mixture was stirred for 6 hours under a nitrogen atmosphere at room temperature. The crude product was purified by column chromatography on silica gel using dichloromethane as eluent. Pale yellow crystals were obtained from slow diffusion of diethyl ether into the dichloromethane solution of the compounds.

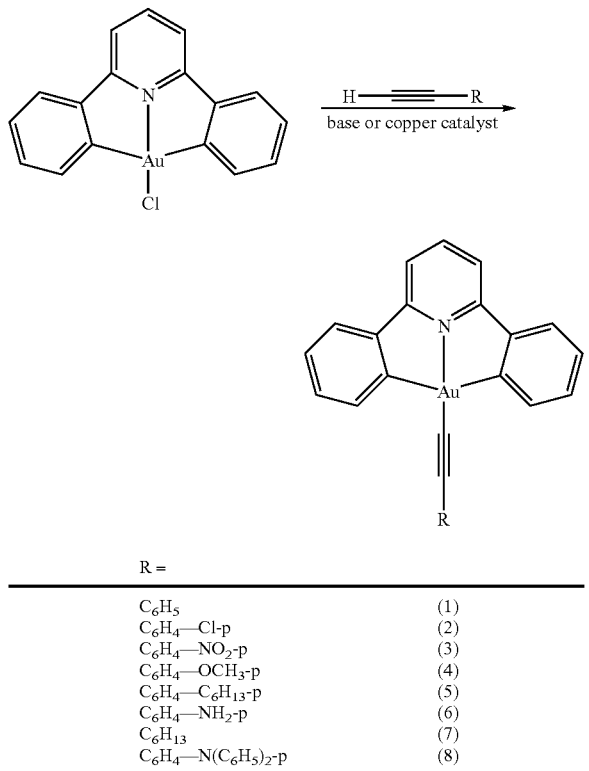

R =

| | |
|---|---|
| $C_6H_5$ | (1) |
| $C_6H_4$—Cl-p | (2) |
| $C_6H_4$—$NO_2$-p | (3) |
| $C_6H_4$—$OCH_3$-p | (4) |
| $C_6H_4$—$C_6H_{13}$-p | (5) |
| $C_6H_4$—$NH_2$-p | (6) |
| $C_6H_{13}$ | (7) |
| $C_6H_4$—$N(C_6H_5)_2$-p | (8) |

The characteristic spectral properties of compounds 1-8 are as follows:

[Au(C^N^C)C≡C—$C_6H_5$]  (Compound 1)

Yield: 88%. $^1$H NMR (300 MHz, $CH_2Cl_2$, 298° K., relative to $Me_4Si$): δ 8.04 (dd, 7.4 and 1.0 Hz, 2 H, C^N^C), 7.92 (t, 8.0 Hz, 1 H, C^N^C), 7.62 (m, 4 H, C^N^C and $C_6H_5$), 7.54 (d, 8.0 Hz, 2 H, C^N^C), 7.26-7.44 (m, 7 H, C^N^C and $C_6H_5$); positive EI-MS: m/z 527 [M]$^+$; IR (KBr): 2147 cm$^{-1}$ ν(C≡C); elemental analyses calc'd for $C_{25}H_{16}NAu$ (found): C 56.93 (56.57), H 3.04 (3.05), N 2.66 (2.66).

[Au(C^N^C)C≡C—$C_6H_4$—Cl-p]  (Compound 2)

Yield: 85%. $^1$H NMR (300 MHz, $CH_2Cl_2$, 298° K, relative to $Me_4Si$): δ 8.00 (dd, 7.2 and 1.0 Hz, 2 H, C^N^C), 7.90 (t, 8.0 Hz, 1 H, C^N^C), 7.50-7.60 (m, 6 H, C^N^C and $C_6H_4$), 7.25-7.42 (m, 6 H, C^N^C and $C_6H_4$); positive EI-MS: m/z 562 [M]$^+$; IR (KBr): 2157 cm$^{-1}$ ν(C≡C); elemental analyses calc'd for $C_{25}H_{15}NClAu·½H_2O$ (found): C 52.59 (52.85), H 2.80 (2.66), N 2.45 (2.40).

[Au(C^N^C)C≡C—$C_6H_4$—$NO_2$-p]  (Compound 3)

Yield: 80%. $^1$H NMR (400 MHz, $CH_2Cl_2$, 298° K., relative to $Me_4Si$): δ 8.22 (d, 9.0 Hz, 2 H, $C_6H_4$), 8.00 (dd, 7.6 and 1.2 Hz, 2 H, C^N^C), 7.94 (t, 8.0 Hz, 1H, C^N^C), 7.73 (d, 9.0 Hz, 2 H, $C_6H_4$), 7.64 (dd, 7.6 and 1.2 Hz, 2H, C^N^C), 7.55 (d, 8.0 Hz, 2H, C^N^C), 7.41 (dt, 7.3 and 1.3 Hz, 2 H, C^N^C), 7.32 (dt, 7.3 and 1.3 Hz, 2 H, C^N^C); positive EI-MS: m/z 572 [M]$^+$; IR (KBr): 2146 cm$^{-1}$ ν(C≡C); elemental analyses calc'd for $C_{25}H_{15}N_2O_2Au$ (found): C 51.64 (51.62), H 2.75 (2.69), N 4.82 (4.75).

[Au(C^N^C)C≡C—$C_6H_4$—$OCH_3$-p]  (Compound 4)

Yield: 86%. $^1$H NMR (400 MHz, $CH_2Cl_2$, 298° K., relative to $Me_4Si$): δ 8.02 (dd, 7.6 and 1.0 Hz, 2 H, C^N^C), 7.90 (t, 8.0 Hz, 1 H, C^N^C), 7.60 (dd, 7.6 and 1.0 Hz, 2 H, C^N^C), 7.50-7.56 (m, 4 H, C^N^C and $C_6H_4$), 7.40 (dt, 7.3 and 1.3 Hz, 2 H, C^N^C), 7.27 (dt, 7.3 and 1.3 Hz, 2 H, C^N^C), 6.91 (d, 8.9 Hz, 2 H, $C_6H_4$), 3.88 (s, 3 H, $OCH_3$); positive EI-MS: m/z 557 [M]$^+$; IR (KBr): 2157 cm$^{-1}$ ν(C≡C); elemental analyses calc'd for $C_{26}H_{18}NOAu·½H_2O$ (found): C 55.12 (55.15), H 3.36 (3.28), N 2.47 (2.48).

[Au(C^N^C)C≡C—$C_6H_4$—$C_6H_{13}$-p]  (Compound 5)

Yield: 75%. $^1$H NMR (300 MHz, $CH_2Cl_2$, 298° K., relative to $Me_4Si$): δ 8.00 (dd, 7.4 and 1.0 Hz, 2 H, C^N^C), 7.87 (t, 8.0 Hz, 1 H, C^N^C), 7.57 (dd, 7.4 and 1.0 Hz, 2 H, C^N^C), 7.47-7.51 (m, 4 H, C^N^C and $C_6H_4$), 7.37 (dt, 7.3 and 1.3 Hz, 2 H, C^N^C), 7.24 (dt, 7.3 and 1.3 Hz, 2 H, C^N^C), 7.18 (d, 8.3 Hz, 2 H, $C_6H_4$), 2.64 (t, 7.7 Hz, 2 H, $CH_2$—$CH_2$—$(CH_2)_3$—$CH_3$), 1.64 (m, 2 H, $CH_2$—$CH_2$—$(CH_2)_3$—$CH_3$), 1.34 (m, 6 H, $CH_2$—$CH_2$—$(CH_2)_3$—$CH_3$), 0.90 (t, 7.0 Hz, 3 H, $CH_2$—$CH_2$—$(CH_2)_3$—$CH_3$); positive EI-MS: m/z 611 [M]$^+$; IR (KBr): 2149 cm$^{-1}$ ν(C≡C); elemental analyses calc'd for $C_{31}H_{28}NAu·½H_2O$ (found): C 60.00 (59.91), H 4.68 (4.60), N 2.26 (2.25).

Au(C^N^C)C≡C—$C_6H_4$—$NH_2$-p]  (Compound 6)

Yield: 80%. $^1$H NMR (300 MHz, $CH_2Cl_2$, 298° K., relative to $Me_4Si$): δ 8.07 (dd, 7.4 and 1.0 Hz, 2 H, C^N^C), 7.92 (t, 8.0 Hz, 1 H, C^N^C), 7.65 (dd, 7.4 and 1.0 Hz, 2 H, C^N^C), 7.56 (d, 8.0 Hz, 2 H, C^N^C), 7.39-7.45 (m, 4 H, C^N^C and $C_6H_4$), 7.30 (dt, 7.5 and 1.3 Hz, 2 H, C^N^C), 6.67 (d, 8.6 Hz, 2 H, $C_6H_4$), 3.84 (s, 2 H, $NH_2$); positive EI-MS: m/z 542 [M]$^+$; IR (KBr): 2143 cm$^{-1}$ ν(C≡C); elemental analyses calc'd for $C_{25}H_{17}N_2Au·½H_2O$ (found): C 54.45 (54.59), H 3.27 (3.13), N 5.08 (5.04).

[Au(C^N^C)C≡C—$C_6H_{13}$]  (Compound 7)

Yield: 85%. $^1$H NMR (300 MHz, $CH_2Cl_2$, 298° K, relative to $Me_4Si$): δ 8.00 (dd, 7.2 and 1.0 Hz, 2 H, C^N^C), 7.90 (t, 8.0 Hz, 1 H, C^N^C), 7.62 (dd, 7.2 and 1.0 Hz, 2 H, C^N^C), 7.53 (d, 8.0 Hz, 4 H, C^N^C), 7.40 (dt, 7.3 and 1.3 Hz, 2 H, C^N^C), 7.28 (dt, 7.3 and 1.3 Hz, 2 H, C^N^C), 2.49 (t, 6.9 Hz, 2 H, $CH_2$—$(CH_2)_2$—$(CH_2)_2$—$CH_3$), 1.63-1.71 (m, 4 H, $CH_2$—$(CH_2)_2$—$(CH_2)_2$—$CH_3$), 1.40 (m, 4 H, $CH_2$—$(CH_2)_2$—$(CH_2)_2$—$CH_3$), 0.95 (t, 7.0 Hz, 3 H, $CH_2$—$(CH_2)_2$—$(CH_2)_2$—$CH_3$); positive EI-MS: m/z 536 [M]$^+$; IR (KBr): 2155 cm$^{-1}$ ν(C≡C); elemental analyses calc'd for $C_{25}H_{24}NAu$ (found): C 56.08 (55.96), H 4.52 (4.60), N 2.62 (2.53).

[Au(C^N^C)C≡C—$C_6H_4$—$N(C_6H_5)_2$-p]  (Compound 8)

Yield: 72%. Yield: 80%. $^1$H NMR (300 MHz, $CH_2Cl_2$, 298° K, relative to $Me_4Si$): δ 8.05 (dd, 7.2 and 1.2 Hz, 2 H, C^N^C), 7.92 (t, 8.0 Hz, 1 H, C^N^C), 7.64 (dd, 7.2 and 1.2 Hz, 2 H, C^N^C), 7.56 (d, 8.0 Hz, 2 H, C^N^C), 7.48 (d, 8.8 Hz, 2 H, C^N^C), 7.42 (t, 7.2 Hz, 2 H, C^N^C H's), 7.32-7.26 (m, 6H, C^N^C, $C_6H_4$ and N—$C_6H_5$), 7.14-7.02 (m, 8H, C^N^C, $C_6H_4$ and N—$C_6H_5$); positive EI-MS: m/z 694 [M]$^+$; IR (KBr): 2143 cm$^{-1}$ ν(C≡C); elemental analyses calc'd for $C_{37}H_{25}N_2Au·½H_2O$ (found): C 60.85 (61.10), H 3.67 (3.53), N 3.78 (3.80).

UV-vis Absorption Properties

Figure 6:
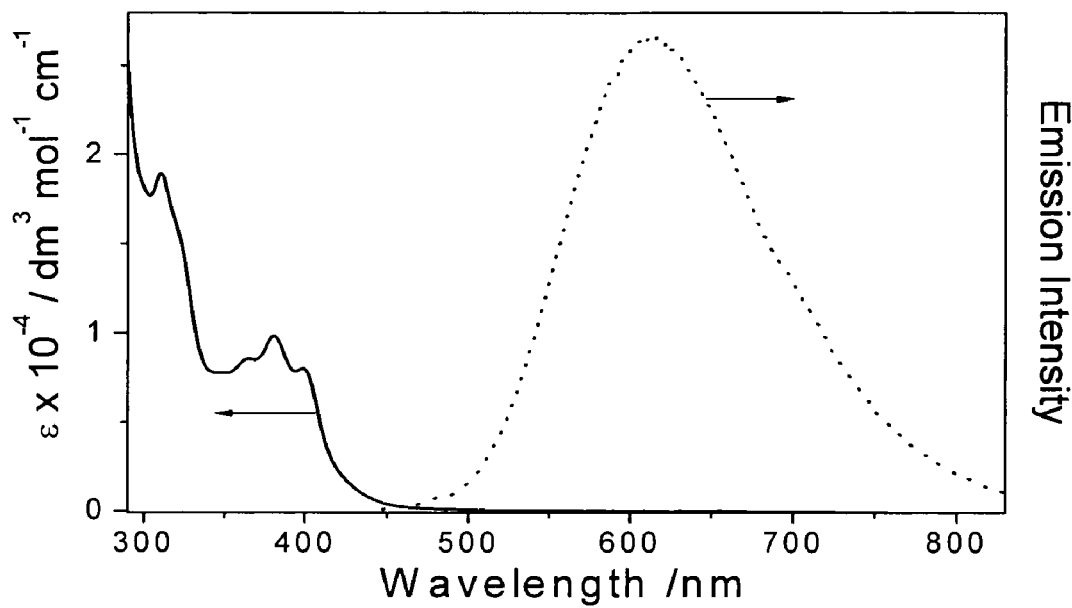
FIG. 6 shows the UV-vis absorption and emission spectra of compound 6 in dichloromethane at 298° K. No instrumental correction was applied for the emission wavelength.
Figure 7:
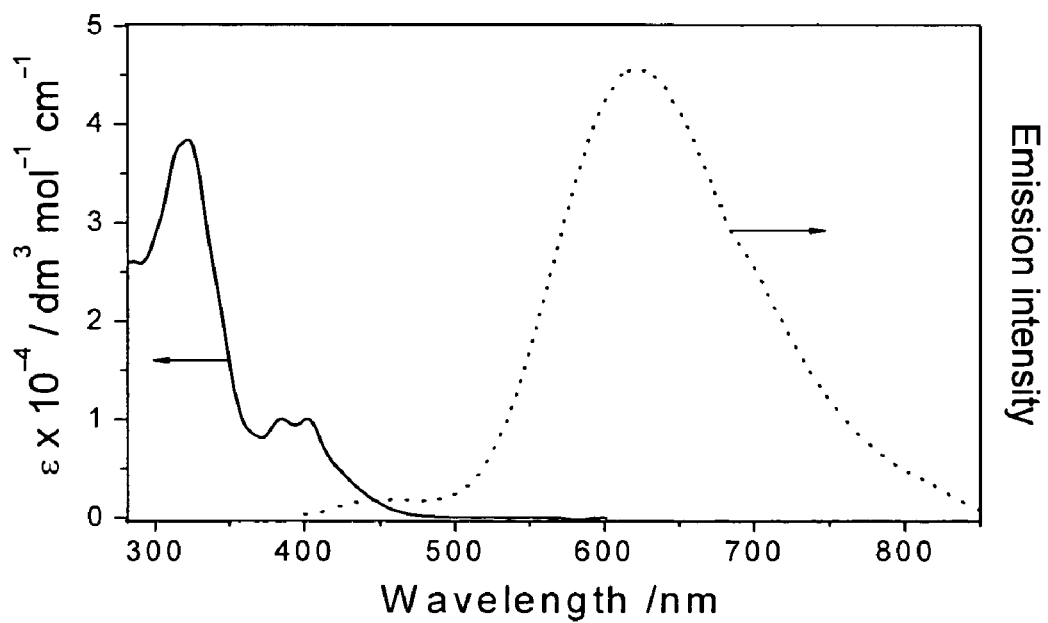
FIG. 7 UV-vis absorption and emission spectra of compound 8 in dichloromethane at 298° K. No instrumental correction was applied for the emission wavelength.
Figure 8:
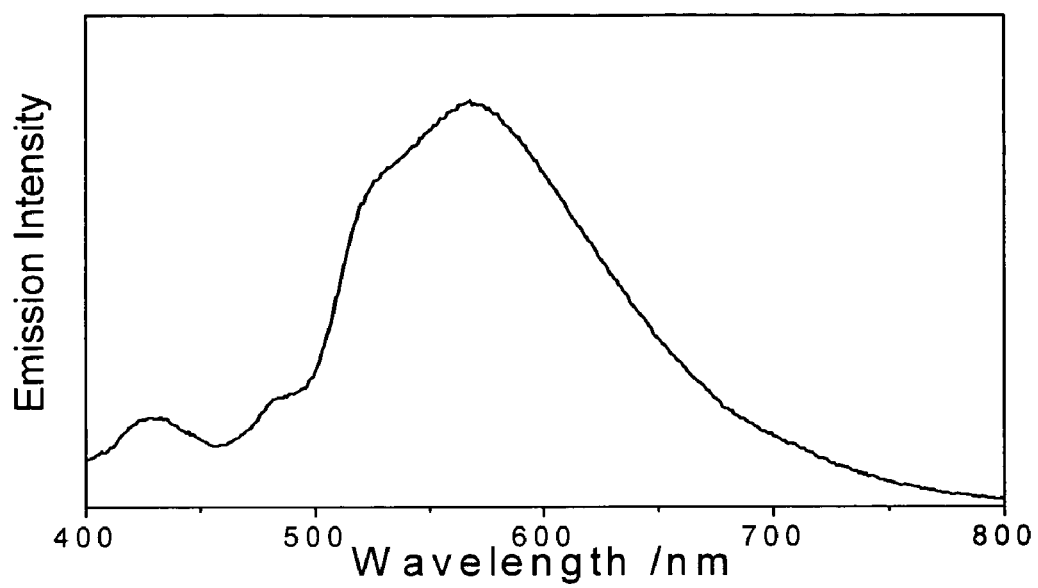
FIG. 8 shows the solid state (thin film) emission spectrum of compound 1 at 298° K. No instrumental correction was applied for the emission wavelength.
Figure 9:
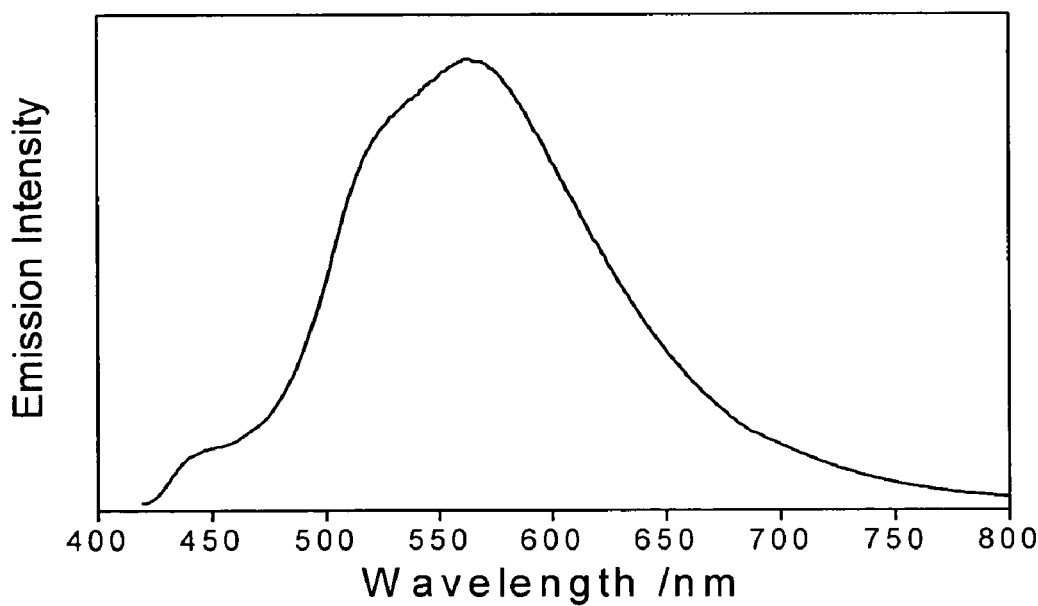
FIG. 9 shows the solid state (thin film) emission spectrum of compound 8 at 298° K. No instrumental correction was applied for the emission wavelength.

All the luminescent gold(III) compounds exhibit an intense absorption band at 312-327 nm and a moderately intense vibronic-structured absorption band at 362-426 nm in dichloromethane at 298° K. The photophysical data of 1-8 are summarized in Table 1. In general, the electronic absorption energies are insensitive to the nature of the alkynyl ligands. The low-energy vibronic-structured absorption band show vibrational progressional spacings of 1310-1380 cm$^{-1}$, corresponding to the skeletal vibrational frequency of the C^N^C ligand. Such low-energy absorptions are assigned as intraligand (IL) $\pi$–$\pi$* transition. An additional shoulder appeared in each of the electronic absorption spectra of compounds 6 and 8 at ca. 415 and 426 nm, respectively (see FIGS. 6 and 7). Since the alkynyl ligand with electron-rich amino substituent has better electron-donating property, the presence of a low-lying alkynyl-to-diarylpyridine ligand-to-ligand charge transfer (LLCT) transition is possible. Thus the low-energy absorptions in compounds 6 and 8 are assigned as an admixture of intraligand (IL) $\pi$–$\pi$*(C^N^C)/LLCT $\pi$ (C≡C—C$_6$H$_4$—NR$_2$-p)→$\pi$*(C^N^C) transition.

Photoluminescence Properties

Figure 2:
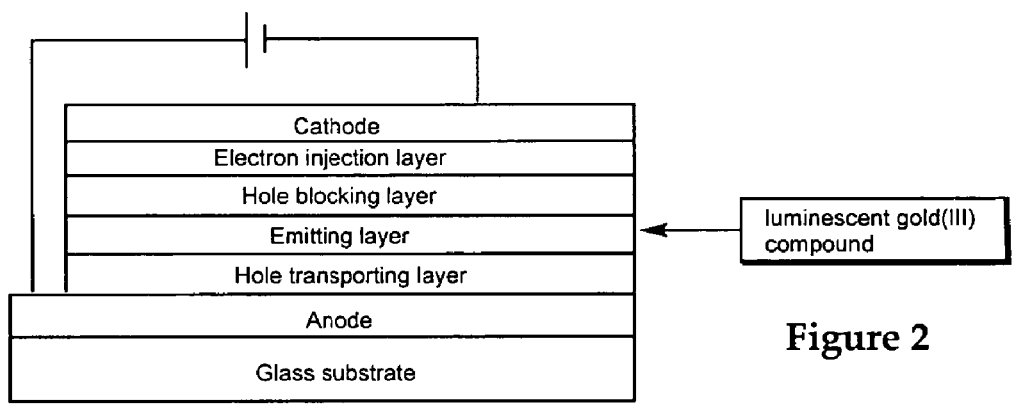
FIG. 2 shows the structure of an OLED using the luminescent compound of the present invention as the light-emitting layer with an electron blocking layer.
Figure 3:
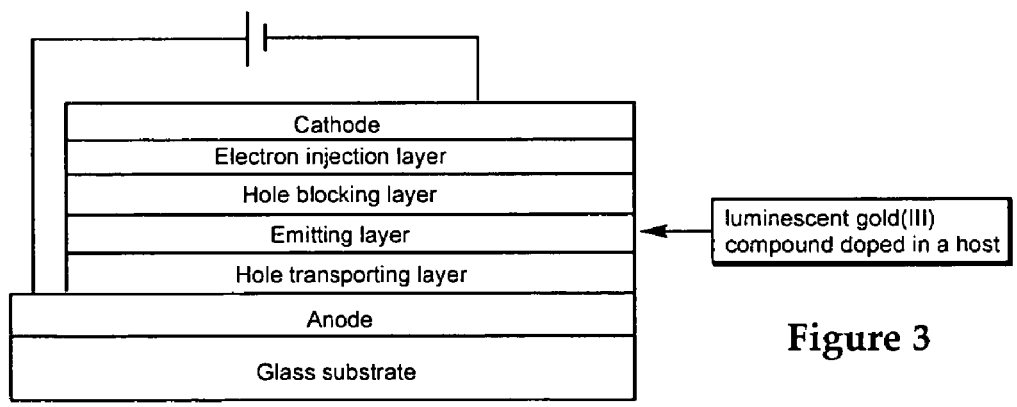
FIG. 3 shows the structure of an OLED using the luminescent copolymer of the present invention as a dopant with an electron blocking layer.
Figure 4:
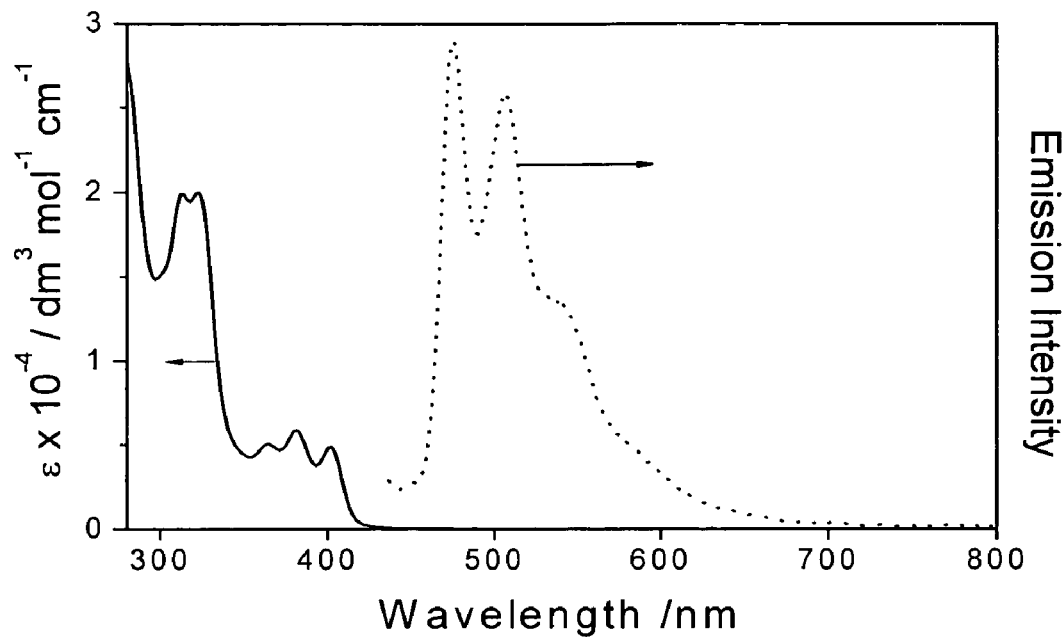
FIG. 4 shows the UV-vis absorption and emission spectra of compound 1 in dichloromethane at 298° K. No instrumental correction was applied for the emission wavelength.
Figure 5:
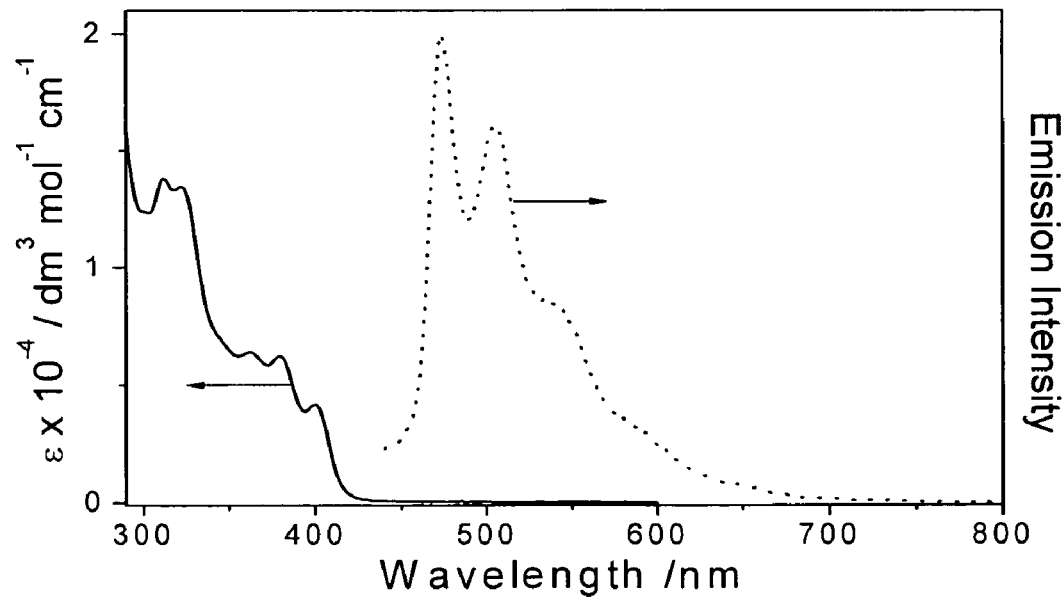
FIG. 5 shows the UV-vis absorption and emission spectra of compound 4 in dichloromethane at 298° K. No instrumental correction was applied for the emission wavelength.

Unlike most other Au(III) compounds which are non-emissive or only show luminescence at low temperature compounds, 1-8 display intense luminescence at 468-625 nm in the solution state at room temperature (Table 1). In general, the emission energies of the compounds were found to be insensitive to the nature of the alkynyl ligands (FIGS. 1 and 2). A vibronic-structured emission band with band maximum at 473 nm is observed for 1-5 and 7 in dichloromethane at room temperature. The vibrational progressional spacings of ca. 1300 cm$^{-1}$ are in line with the C≡C and C≡N stretching frequency of the tridentate ligand, indicative of the involvement of tridentate ligand in the excited state origin. Similar to the low-energy absorption band in the electronic absorption studies, the luminescence is assigned as originated from metal-perturbed intra-ligand $^3$[$\pi$–$\pi$*] state of the tridentate C^N^C ligand. Compounds 6 and 8 exhibit a structureless emission band at lower energy in dichloromethane at room temperature (FIGS. 3 and 4). The emission spectra of compounds 1-8 in the solid state show a low-energy structureless band at around 570 nm (FIGS. 4 and 5). The red shift of the solid-state emission relative to that in the solution state is attributed to the excimeric intraligand emission arising from the $\pi$ stacking of the C^N^C ligand, probably due to the ordered packing of the molecules in the solid state.

TABLE 1

Photophysical data for Compounds 1 through 8.

| Compound | Medium (T[K]) | Absorption $\lambda$max [nm] ($\epsilon$max[dm$^3$mol$^{-1}$cm$^{-1}$]) | Emission $\lambda$max [nm] |
|---|---|---|---|
| 1 | CH$_2$Cl$_2$ (298) | 312 (19890), 322 (19980), 364 (5050), 381 (5870), 402 (4870) | 476, 506, 541, 582 |
| | Solid (298) | | 588 |
| | Thin film (298)$^a$ | | 568 |
| 2 | CH$_2$Cl$_2$ (298) | 312 (19400), 322 (19640), 365(4640), 382(5170), 402(4305) | 476, 506, 539, 584 |
| | Solid (298) | | 558 |
| 3 | CH$_2$Cl$_2$ (298) | 312 sh (27160), 327 (36005), 364 sh (17995), 382 sh (10170), 403 (5630) | 477, 508, 546, 593 |
| | Solid (298) | | 563 |
| 4 | CH$_2$Cl$_2$ (298) | 312 (13820), 322 (13455), 362 (6400), 380 (6245), 400 (4190) | 474, 505, 539, 584 |
| | Solid (298) | | 555 |
| 5 | CH$_2$Cl$_2$ (298) | 312 (17855), 322 (18100), 363 (5785), 381 (5945), 401 (4455) | 475, 505, 538, 583 |
| | Solid (298) | | 556 |
| 6 | CH$_2$Cl$_2$ (298) | 310 (19195), 322 sh (15680), 365 (8855) 381 (10100), 399 (8300), 415 sh (3410) | 611 |
| | Solid (298) | | 585 |
| 7 | CH$_2$Cl$_2$ (298) | 311 (14775), 320 (13925), 364 (3810), 380 (4900), 400 (4280) | 473, 505, 537, 583 |
| | Solid (298) | | 555 |
| 8 | CH$_2$Cl$_2$ (298) | 312 (37090), 322 (38325), 364 (8525), 384 (10040), 400 (10035), 426 sh (4145) | 625 |
| | Thin film (298)$^a$ | | 564 |

$^a$prepared by vacuum deposition

EXAMPLE 2

Figure 10A:
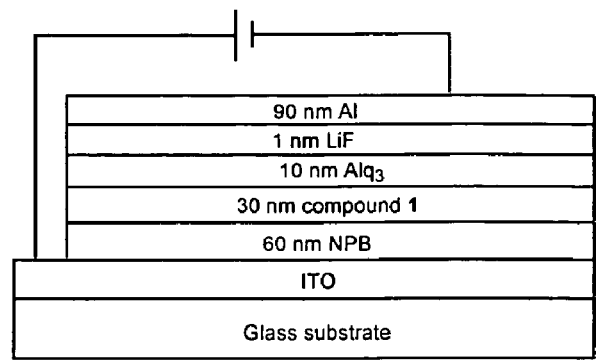
FIG. 10A shows the multilayer OLED with the structure of ITO/NPB (60 nm)/compound 1 (30 nm)/Alq$_3$ (10 nm)/LiF (1 nm)/Al (90 nm).
Figure 10B:
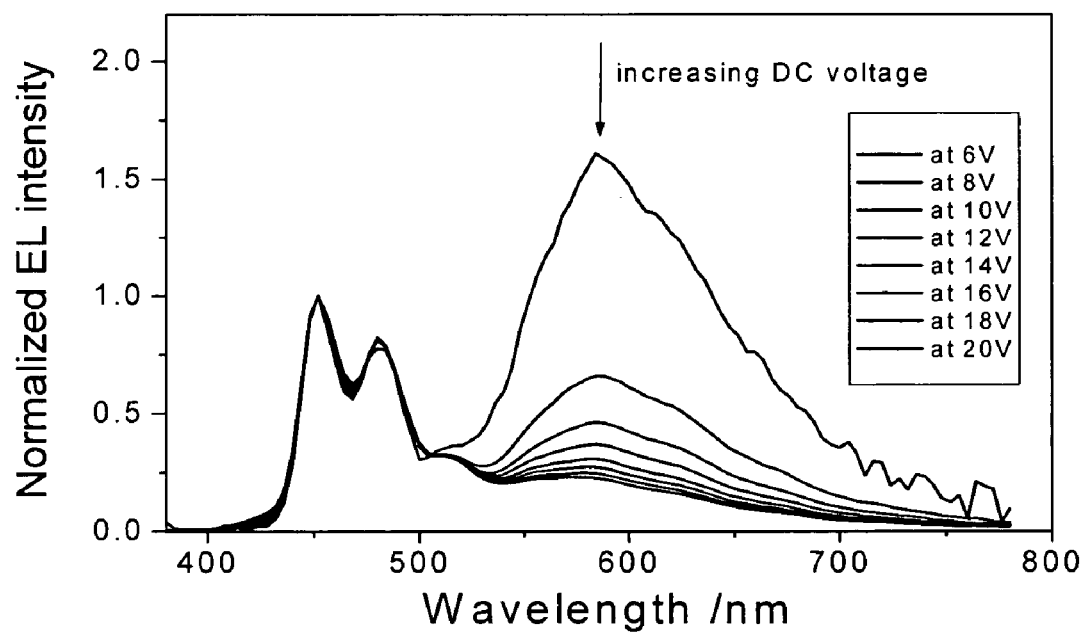
FIG. 10B shows the electroluminescence spectra of device 1 (see FIG. 1) at different applied DC voltages; the emission intensities are normalized in the range of 450-480 nm.

FIG. 10A shows an illustrative OLED structure of device 1: ITO/4,4'-bis[N-(1-naphtyl)-N-phenyl-amino]biphenyl (NPB) (60 nm)/compound 1 (30 nm)/aluminum tris(8-hydroxyquinoline) (Alq$_3$) (10 nm)/LiF (1 nm)/Al (90 nm). NPB and Alq$_3$ act as the hole transporting material and the electron transporting or injection material, respectively. Electroluminescence spectra of device 1 at different DC voltages applied are shown in FIG. 10B. In general, both the emission band of NPB in the range of 450-520 nm and the emission band of compound 1 at about 585 nm are observed upon application of DC voltage. At a lower DC voltage, the emission arising from compound 1 is more intense relative to the emission band of NPB. Upon increasing the DC voltage, the relative emission intensity ratio of compound 1: NPB decreases gradually. Therefore, the emission color of device 1 can be tuned from orange to green by applying different DC voltages.

EXAMPLE 3

Figure 11A:
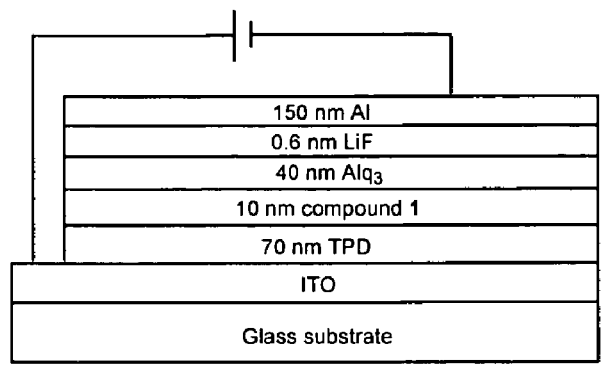
FIG. 11A shows the multilayer OLED of device 2 (see FIG. 2) with the structure of ITO/TPD (70 nm)/compound 1 (10 nm)/Alq$_3$ (40 nm)/LiF (0.6 nm)/Al (150 nm).
Figure 11B:
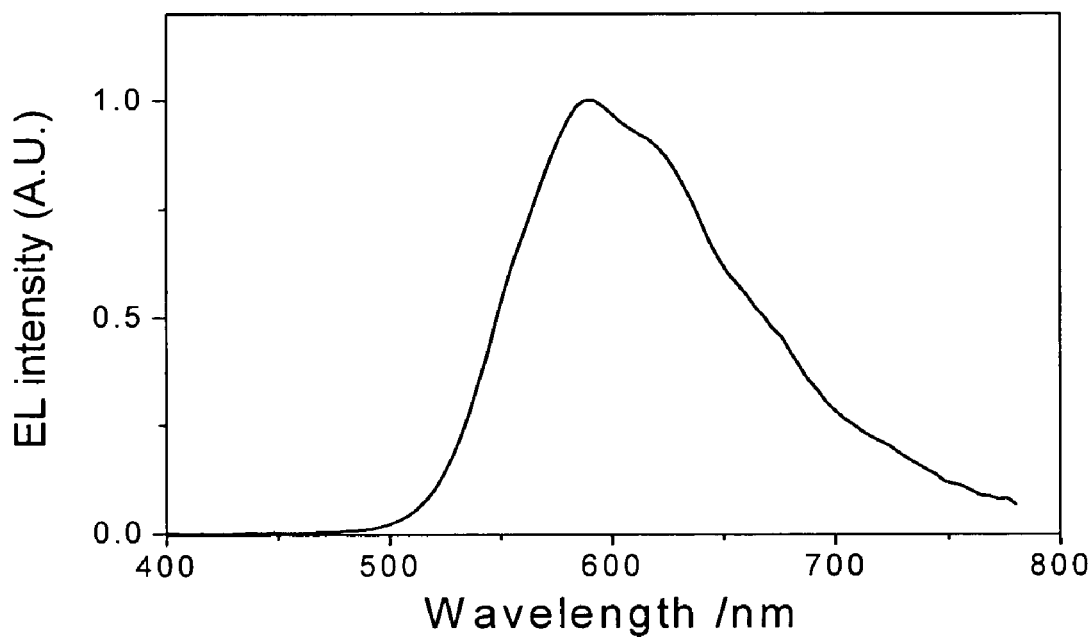
FIG. 11B shows the electroluminescence spectrum of device 2 (see FIG. 2) upon applying 7 V DC voltage.
Figure 11C:
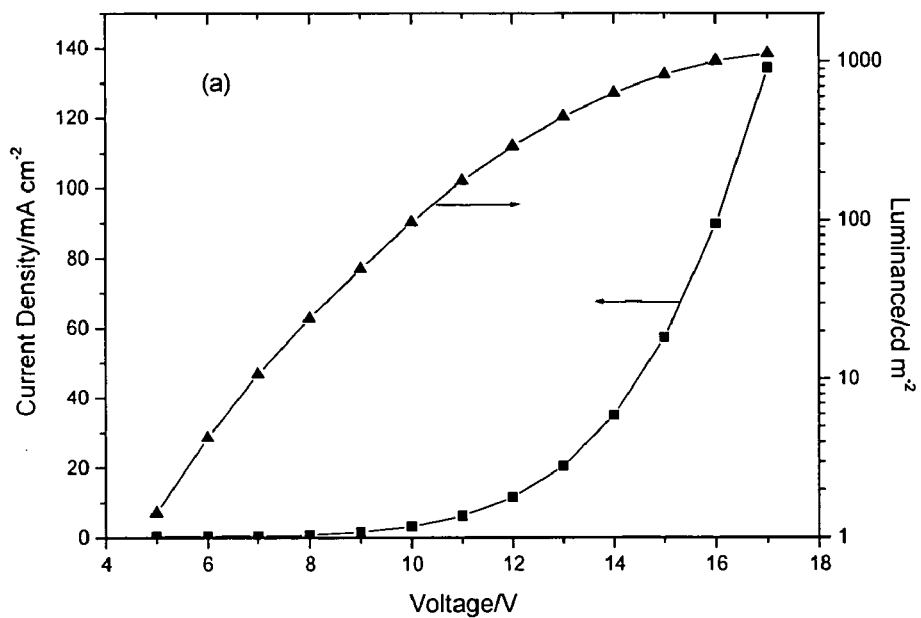
FIG. 11C shows the current density and luminance versus voltage characteristics of device 2 (see FIG. 2).
Figure 11D:
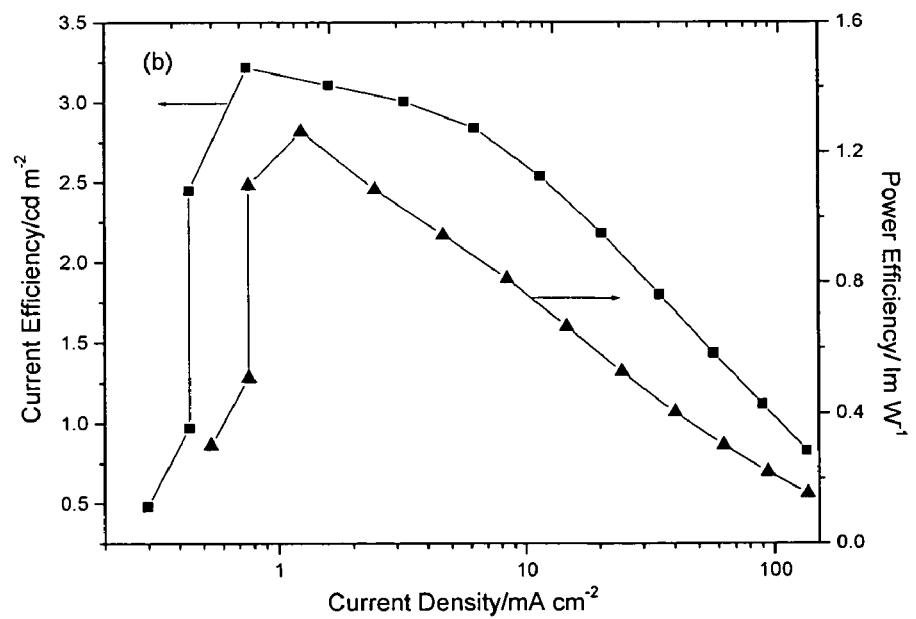
FIG. 11D shows the current and power efficiency versus current density characteristics of device 2 (see FIG. 2).

FIG. 11A shows an illustrative OLED structure of device 2: ITO/N,N'-diphenyl-N,N'-bis(3-methylphenyl)-[1,19-biphenyl]-4,4'-diamine (TPD) (70 nm)/compound 1 (10 nm)/Alq$_3$ (40 nm)/LiF (0.6 nm)/Al (150 nm). TPD acts as the hole transporting material. The electroluminescence spectrum of device 2 is depicted in FIG. 11B. The EL spectrum shows only one band at around 585 nm. The EL spectrum compares well with the photoluminescence (PL) spectrum of compound 1 (FIG. 7), indicating that both EL and PL arise from the same excited state or the same type of exciton, which is attributed to the excimeric intraligand emission resulting from the $\pi$ stacking of the C^N^C ligand. FIGS. 11C and 11D show the characteristics of device 2 with the relationship between current density, luminance and voltage; and between current, power efficiency and current density. The turn-on voltage is about 5 V.

EXAMPLE 4

Figure 12A:
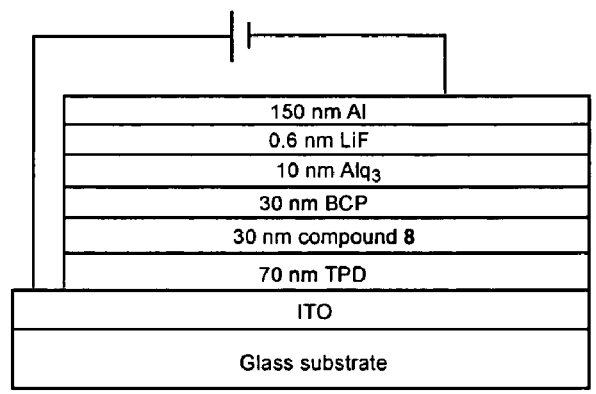
FIG. 12A shows the multilayer OLED with the structure of device 3 (see FIG. 3) ITO/TPD (70 nm)/compound 8 (30 nm)/BCP (30 nm)/Alq$_3$ (10 nm)/LiF (0.6 nm)/Al (150 nm).

FIG. 12A shows an illustrative OLED structure of device 3: ITO/TPD (70 nm)/compound 8 (30 nm)/2,9-dimethyl-4,7-diphenyl-1,10-phenathroline (BCP) (30 nm)/Alq$_3$ (10 nm)/

Figure 12B:
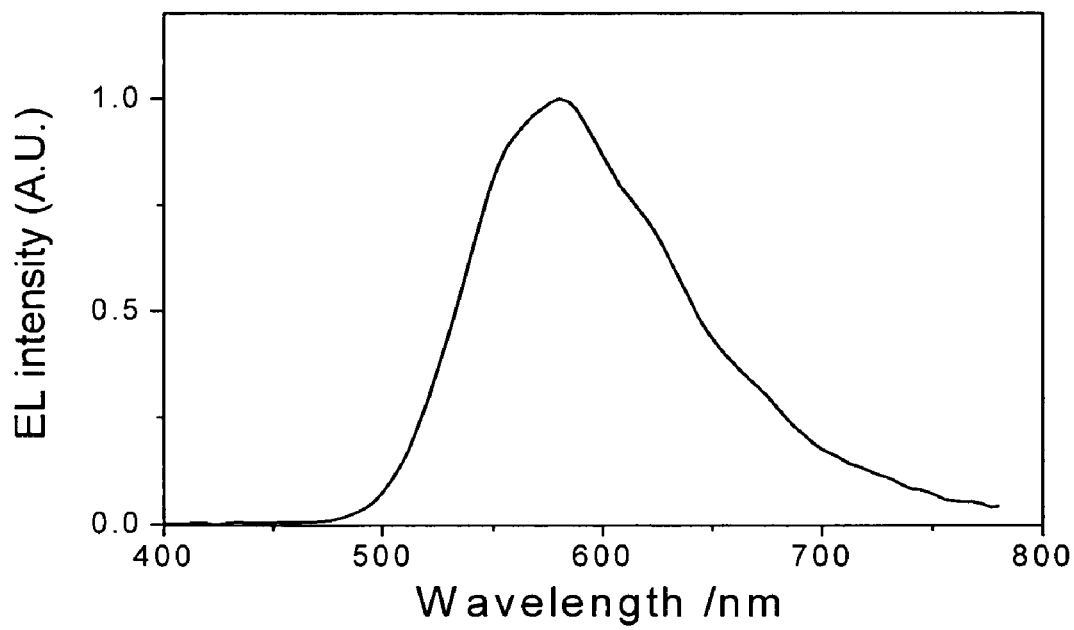
FIG. 12B shows the electroluminescence spectrum of device 3 (see FIG. 3) upon applying 9 V DC voltage.
Figure 12C:
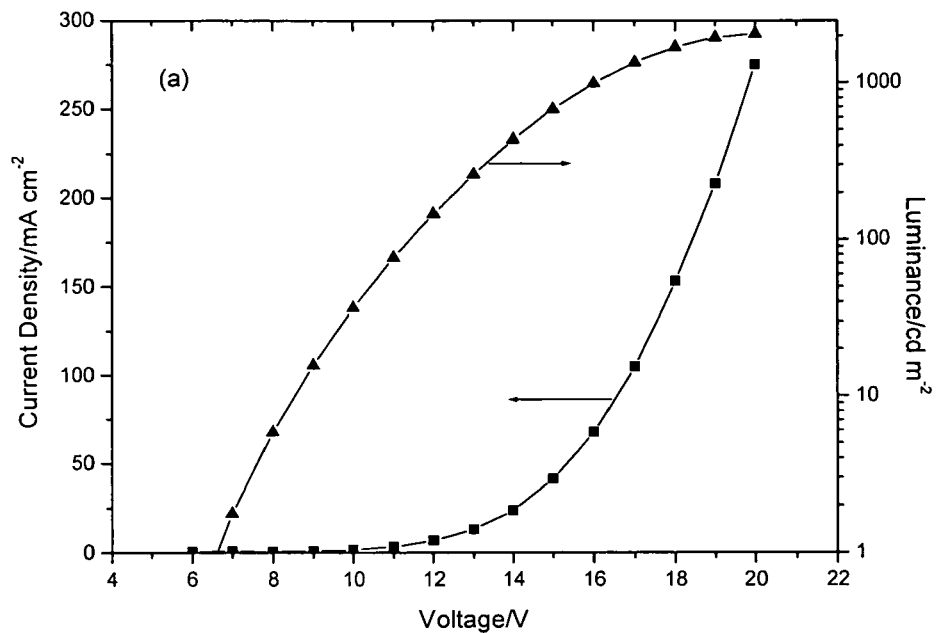
FIG. 12C shows the current density and luminance versus voltage characteristics of device 3 (see FIG. 3).
Figure 12D:
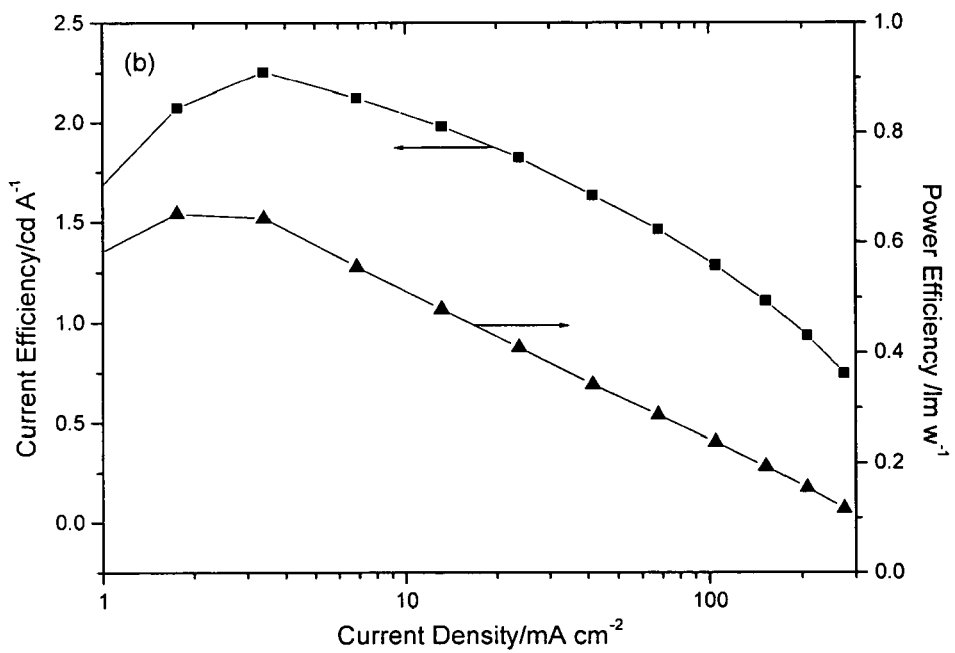
FIG. 12D shows the current and power efficiency versus current density characteristics of device 3 (see FIG. 3).

LiF (0.6 nm)/Al (150 nm). BCP acts as the hole blocking material. The electroluminescence spectrum of device 3 is depicted in FIG. 12B. The EL spectrum shows only one band at around 580 nm. The EL spectrum compares well with the photoluminescence (PL) spectrum of compound 8 (shown in FIG. 5), indicating that both EL and PL arise from the same excited state or the same type of exciton, which is attributed to the excimeric intraligand emission resulting from the 7 stacking of the C^N^C ligand. FIGS. 12C and 12D show the characteristics of device 3 with the relationship between current density, luminance and voltage; and between current, power efficiency and current density. The turn-on voltage is about 6.5 V. The relatively higher turn on voltage is due to the increase in emitting layer thickness (30 nm) and the introduction of an additional hole blocking layer.

EXAMPLE 5

Figure 13A:
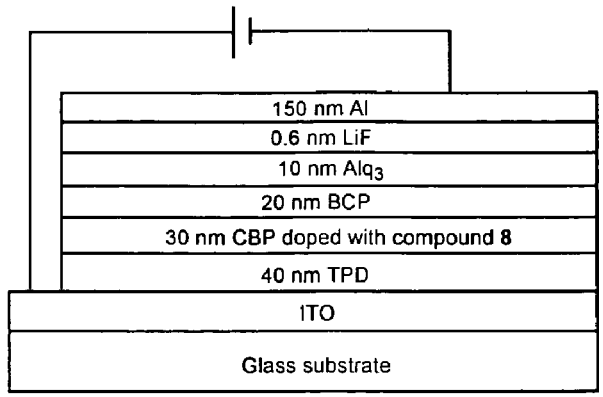
FIG. 13A shows the multilayer OLED of device 4 with the structure: ITO/TPD (40 nm)/CBP doped with (X %) compound 8 (30 nm)/BCP (20 nm)/Alq$_3$ (10 nm)/LiF (0.6 nm)/Al (150 nm) [X=1 (device 4a), 3 (device 4b), 6 (device 4c), 12 (device 4d), 18 (device 4e), 100 (device 4f)].
Figure 13B:
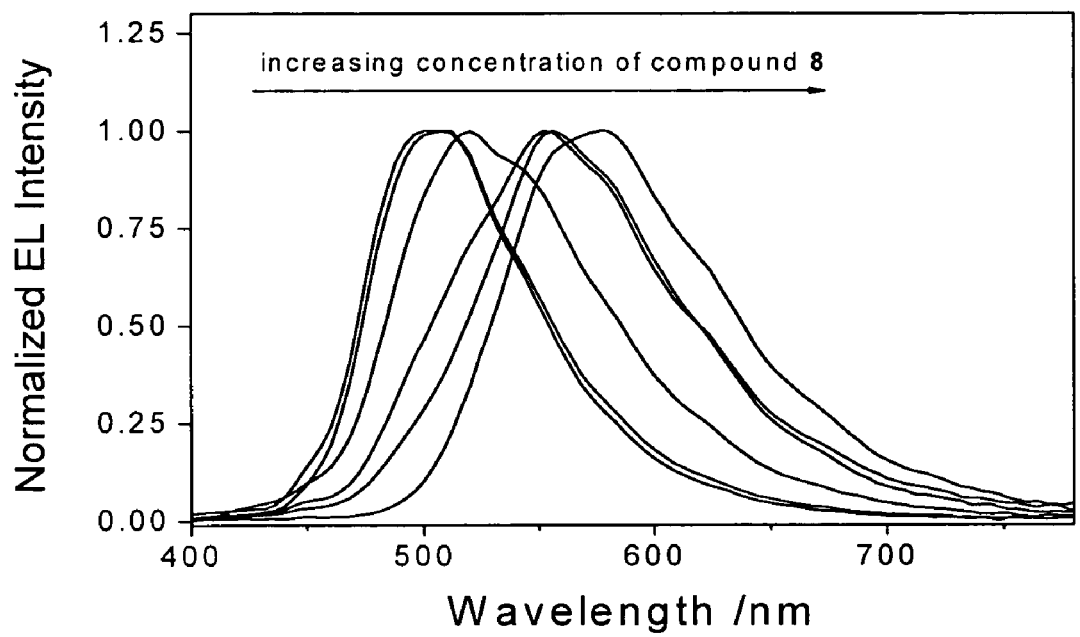
FIG. 13B shows normalized electroluminescence spectra of devices 4a-f with different concentrations of compound 81% (device 4a), 3 (device 4b), 6 (device 4c), 12 (device 4d), 18 (device 4e), 100 (device 4f) as dopant upon applying 12 V DC voltage.
Figure 14A:
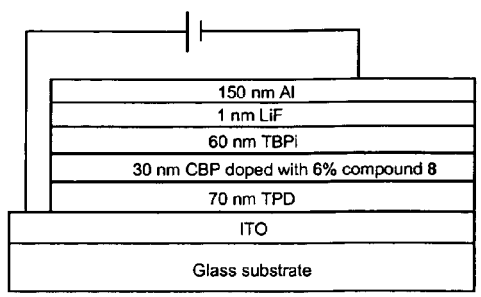
FIG. 14A shows device 5: ITO/TPD (70 nm)/CBP (compound 8, 6 wt %) (30 nm)/TPBi (60 nm)/LiF (1 nm)/Al (150 nm).
Figure 14B:
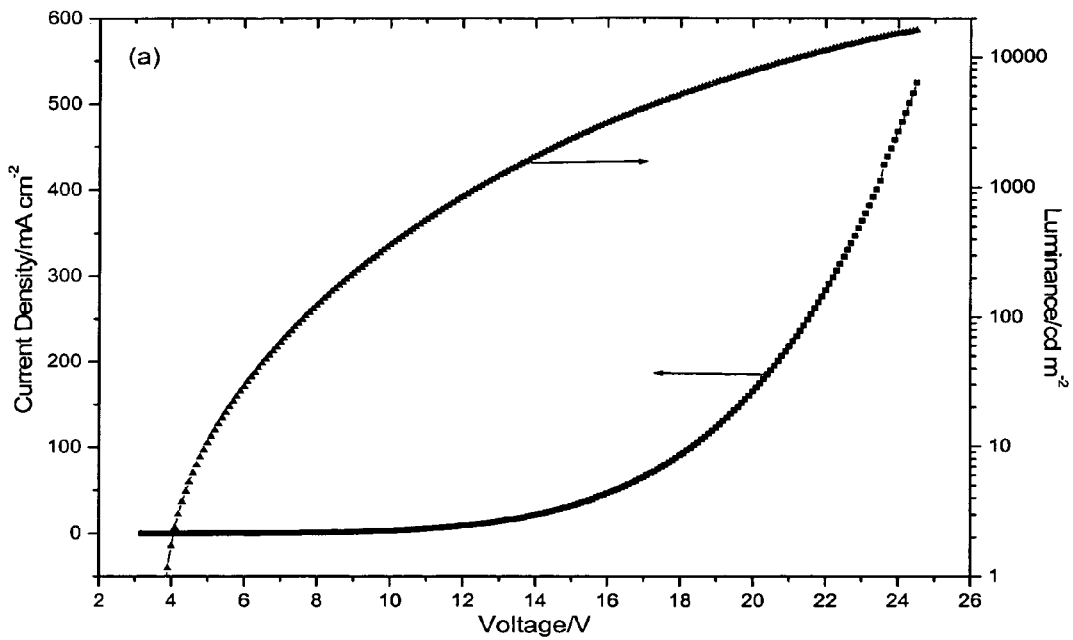
FIG. 14B shows a plot of current density and luminance versus voltage for device 5.
Figure 14C:
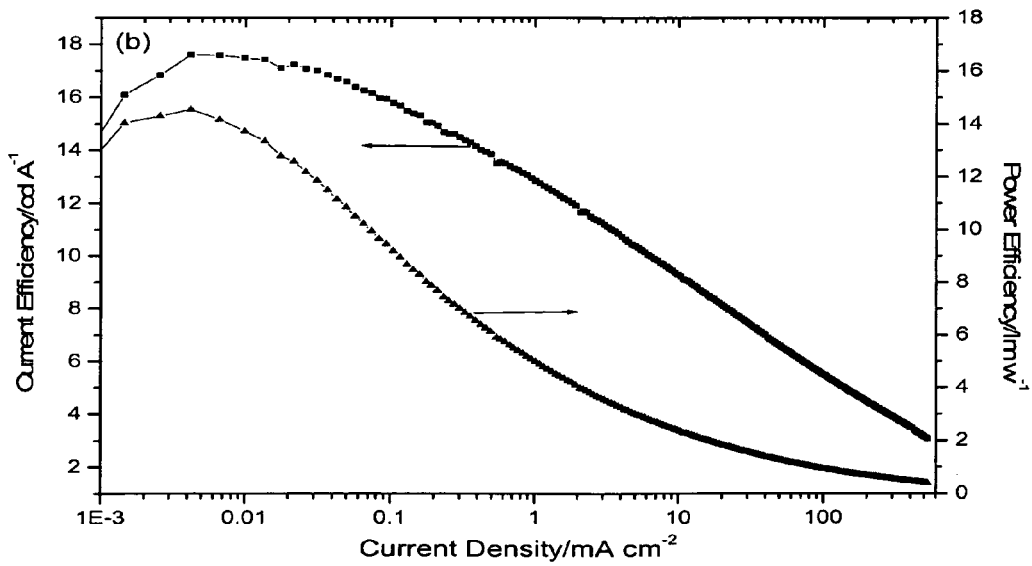
FIG. 14C shows a plot of current and power efficiency versus current density for device 5.
Figure 14D:
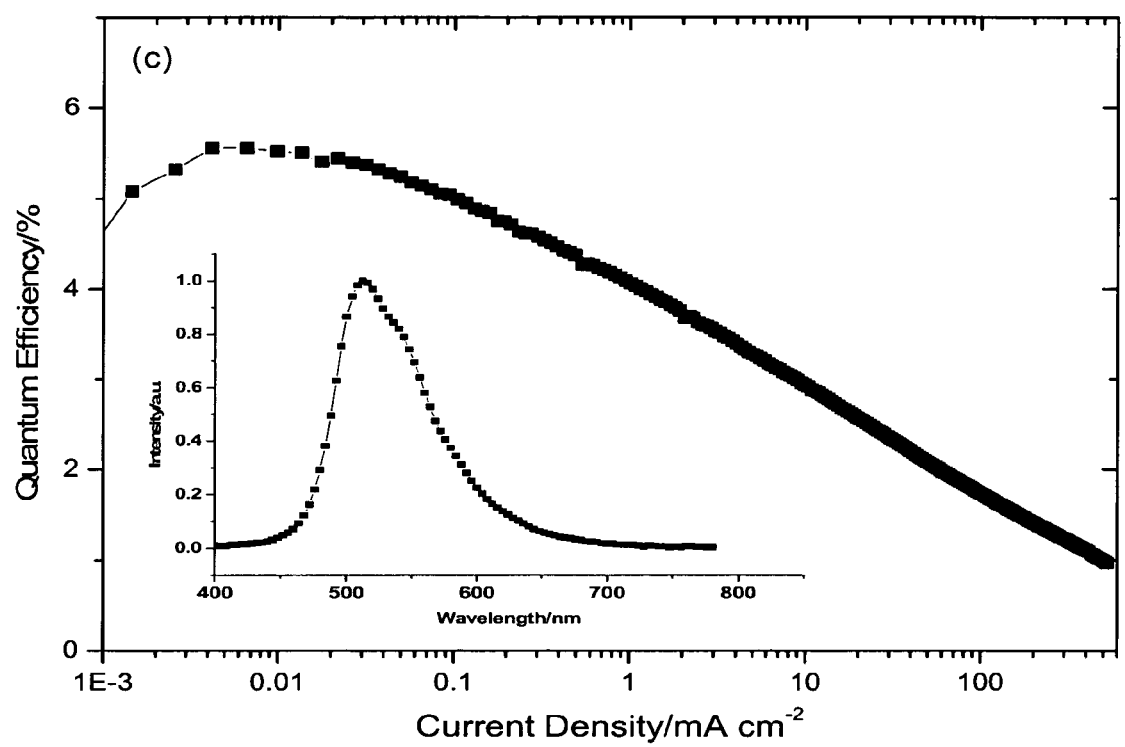
FIG. 14D plot of quantum efficiency versus current density. Inset: spectra characteristics of device 5.

FIG. 13A shows the general OLED structure: ITO/TPD (70 nm)/4,4'-N,N'-dicarbazole-biphenyl (CBP) doped with (X %) compound 8 (30 nm)/BCP (30 nm)/Alq$_3$ (10 nm)/LiF (0.6 nm)/Al (150 nm) [X=1 (device 4a), 3 (device 4b), 6 (device 4c), 12 (device 4d), 18 (device 4e), 100 (device 4f)]. CBP acts as the host material. FIG. 13B displays the normalized EL spectra of devices 4a-f with different concentration of compound 8 as dopant upon applying 12 V DC voltage. It is clear that the EL band shifts to red from 500 nm to 580 mm upon increasing the dopant concentration. Since the emitting layer in device 4 is fabricated by the simultaneous vacuum deposition of compound 8 and the host, a higher dopant concentration of compound 8 may give rise to a higher order and better packing of the molecules, leading to stronger π stacking of the C^N^C ligand, and hence a lower energy excimeric intraligand emission. Therefore, a dependence of the EL color on the dopant concentration of the luminescent gold(III) compound, leading to concentration-dependent color tuning, can be accomplished in the present invention.

EXAMPLE 6

Device 5 with the following OLED structure: ITO/TPD (70 nm)/CBP (compound 8, 6 wt %) (30 nm)/1,3,5-tris(2'-(1'-phenyl-1'-H-benzimidazole)benzene (TPBi) (60 nm)/LiF (1 nm)/Al (150 nm) is fabricated (FIG. 13). Higher efficiency is obtained in device 5 by using TPBi as electron transporting material which has higher mobility than Alq$_3$. The characteristics of device 5 are illustrated in FIG. 13B which shows (a) plot of current density and luminance versus voltage; (b) plot of current and power efficiency versus current density; and (c) plot of quantum efficiency versus current density. Inset: spectra characteristics of device 5.

The invention claimed is:
1. A luminescent compound having the following structure:

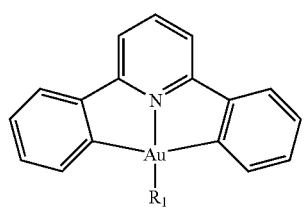

wherein R$_1$ is an alkynyl or substituted alkynyl group.

2. A luminescent compound according to claim 1, wherein the compound can be deposited as a thin layer.

3. A luminescent compound according to claim 2, wherein the thin layer can be deposited by sublimation, vacuum deposition, or spin-coating/printing.

4. A luminescent compound according to claim 1, wherein the compound has photoluminescent properties.

5. A luminescent compound according to claim 4, wherein the compound has electroluminescent properties.

6. A luminescent compound of claim 1, wherein the compound can be fabricated into a light-emitting device.

7. A luminescent compound of claim 1, wherein the compound serves as the light-emitting layer of a light emitting device.

8. A luminescent compound of claim 1, wherein the compound serves as a dopant in the light-emitting layer of a light-emitting device.

9. A luminescent compound of claim 7, wherein the luminescent color of the compound varies with the applied voltage.

10. A luminescent compound of claim 8, wherein energy of the compound varies with the concentration of the dopant.

11. A method for preparing a luminescent compound with a tridentate ligand and at least one strong σ-donating group coordinating to a gold(III) metal center, comprising the following reaction:

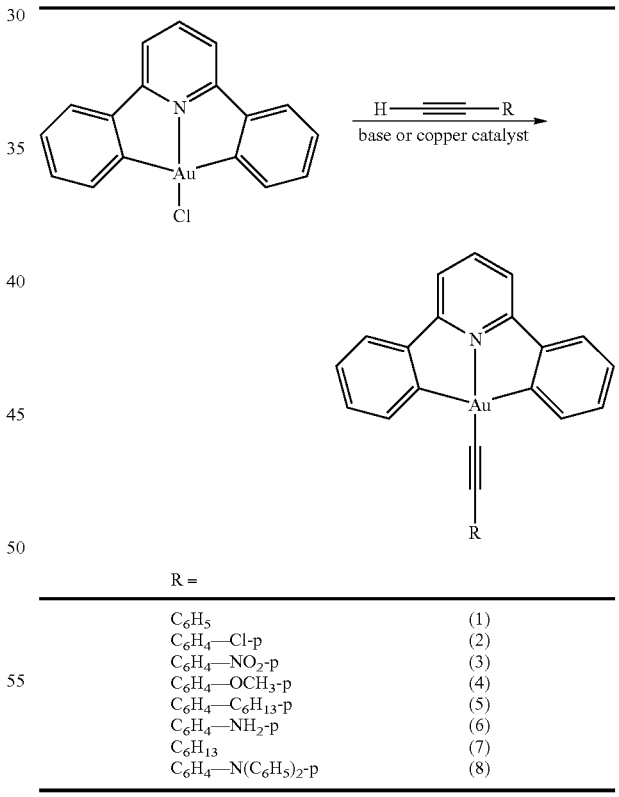

| R = | |
|---|---|
| C$_6$H$_5$ | (1) |
| C$_6$H$_4$—Cl-p | (2) |
| C$_6$H$_4$—NO$_2$-p | (3) |
| C$_6$H$_4$—OCH$_3$-p | (4) |
| C$_6$H$_4$—C$_6$H$_{13}$-p | (5) |
| C$_6$H$_4$—NH$_2$-p | (6) |
| C$_6$H$_{13}$ | (7) |
| C$_6$H$_4$—N(C$_6$H$_5$)$_2$-p | (8) |

12. A luminescent compound prepared according to the method of claim 11.

13. A light emitting device comprising a layer of a luminescent compound prepared according to the method of claim 11.

14. A light emitting device comprising a layer of the luminescent compound of claim 1.

15. A dopant comprising a compound according to claim 1.

16. A dopant comprising a compound according to claim 12.

17. A light emitting device having a light emitting layer comprising the compound of claim 1.

18. A light emitting device having a light emitting layer comprising a compound prepared according to the method of claim 11.

* * * * *